US006656257B2

(12) United States Patent
Cohen

(10) Patent No.: US 6,656,257 B2
(45) Date of Patent: Dec. 2, 2003

(54) GRIPPING COMPOSITION AND METHOD OF PREPARING THE SAME

(75) Inventor: Robert S. Cohen, Dover, OH (US)

(73) Assignee: Mighty Grip, Inc., Scottsdale, AZ (US)

( * ) Notice: Subject to any disclaimer, the term of this patent is extended or adjusted under 35 U.S.C. 154(b) by 0 days.

(21) Appl. No.: 10/072,899

(22) Filed: Feb. 12, 2002

(65) Prior Publication Data

US 2003/0150357 A1 Aug. 14, 2003

(51) Int. Cl.$^7$ .............................. C09K 3/14; C09K 3/18
(52) U.S. Cl. .................... 106/36; 106/272; 106/285; 424/724; 424/684; 427/201
(58) Field of Search .................... 106/36, 272, 285, 106/482, 416, 486, 487, 484; 424/724, 684; 427/201

(56) References Cited

U.S. PATENT DOCUMENTS

| | | | |
|---|---|---|---|
| 3,035,988 A | * | 5/1962 | Cohen ........................ 427/4 |
| 3,915,728 A | | 10/1975 | Saad et al. |
| 4,572,690 A | | 2/1986 | Savanuck |
| 4,593,764 A | * | 6/1986 | Lilienthal .................. 166/312 |
| 5,204,088 A | | 4/1993 | Noebel et al. |
| 5,219,465 A | * | 6/1993 | Goertz et al. ................. 71/28 |
| 5,364,464 A | | 11/1994 | Sereboff |
| 5,565,023 A | | 10/1996 | Sereboff |
| 5,886,089 A | | 3/1999 | Knowlton |
| 6,034,163 A | * | 3/2000 | Barbee et al. .............. 524/445 |
| 6,048,612 A | | 4/2000 | Dozier |
| 6,177,171 B1 | | 1/2001 | Constantinides |
| 6,271,185 B1 | | 8/2001 | Kodali et al. |

* cited by examiner

*Primary Examiner*—Michael Marcheschi
(74) *Attorney, Agent, or Firm*—Finnegan, Henderson, Farabow, Garrett & Dunner, L.L.P.

(57) ABSTRACT

A composition for improving grip between the hands and a tool or implement is provided, which comprises a chlorinated paraffin, a dispersing agent, and a solvent in an amount up to and including about 3.0% by weight relative to the total weight of the composition. A method of making the composition in the form of a dry powder, as well as a method of using the dry powder to improve friction or grip on the hands, are also provided.

22 Claims, No Drawings

GRIPPING COMPOSITION AND METHOD OF PREPARING THE SAME

TECHNICAL FIELD

This invention relates to a composition for use as a friction or grip enhancing agent to be applied to the hands of athletes, and the like, who handle the tools of their activities and trades, and require that their grip be sure. The inventive friction or grip enhancing agent can also be used in household or commercial uses, including in the corrugation (boxing) and banking industries.

BACKGROUND OF THE INVENTION

The gripping portion of tools and sporting equipment is generally made of hard materials that may become difficult to grasp when wetted, particularly by perspiration. In an attempt to improve the ability to grip such tools, therefore, various materials that can be applied to the hand or the implement to be gripped have been developed. For example, the rosin bag is a traditional piece of equipment generally being used both by a pitcher and a hitter in a ball game to make more certain of their grip on the ball and the bat, respectively. Similarly, tennis and golf players can require a light application of powdered rosin to their hands to aid in making their grips more certain. The fundamental disadvantages of such prior art compositions, however, is their lack of staying power, permanence and relatively poor effectiveness. Perspiration on the bare hands of an athlete, for example, can easily dislodge the rosin dust, which requires the frequent reapplication of rosin. To avoid these and analogous inherent drawbacks, the prior art describes different materials that purportedly improve gripping characteristics.

For example, U.S. Pat. Nos. 5,565,023 and 5,364,464 to Sereboff et al. are illustrative of frictional grip enhancing compositions that comprise an inorganic powder, such as magnesium or calcium carbonate or magnesium silicate, and sawdust particles. Similarly, U.S. Pat. No. 4,572,690 to Savanuck relates to a gripping composition primarily comprising an inorganic oxide and minor amounts of an astringent, for example, aluminum chlorohydrate. Such compositions are taught for use in rosin bags.

In addition to the dry compositions described above, the prior art describes compositions in the form of a liquid, which are allowed to dry on the surface of the hands or the substrate to which the compositions are applied. For example, U.S. Pat. No. 5,886,089 to Knowlton relates to a grip and friction enhancement composition that comprises an aqueous mixture of a fluoroalkyl acrylate copolymer emulsion and a silicone polymer micro emulsion. The aqueous mixture described in this patent is applied to a surface, where it is allowed to dry into a film that is only a partially cross-linked fluoroalkyl copolymer. In addition, U.S. Pat. No. 5,204,088 to Noebel relates to the application of a coating of hydrophobic silica particles onto one's hands or onto athletic equipment where an improved grip is desired. Noebel teaches dispersing the hydrophobic silica particles in large amounts of a volatile solvent for use in an aerosol dispenser.

In addition to improved gripping compositions, the prior art further describes complete articles or systems for improving gripping characteristics. U.S. Pat. No. 6,177,171 to Constantinides, for example, is directed to a shear force modulation system which controls friction between the skin and an abrasive surface. The mechanical system disclosed in this patent comprises upper and lower pads and slides, with an elastic connector attaching the upper pad and the lower pad. U.S. Pat. No. 6,048,612 to Dozier relates to an article for enhancing the grasping of an athletic implement grip. The article described in this reference comprises a carrier material that is impregnated with a tacky adhesive, such as ditridecylphthalate, and a thickener, such as polyethylene glycol fatty acid. A wetting agent, such as dodecyl benzene, may be added to the mixture of adhesive and thickener to facilitate impregnating mixture into the carrier. Problems associated with the tacky adhesive type of composition described in Dozier include transfer of the adhesive to unwanted surfaces, such as clothes, and the accumulation of dirt, grass, and the like on both the hands and the implement to be gripped.

To avoid the inherent drawbacks associated with prior art compositions not having a need for large amounts of solvent, or the use of cumbersome mechanical systems as discussed above, the present invention is directed to a friction and gripping composition comprising a dry powder which exhibits improved, friction, gripping, and staying power or retention properties.

SUMMARY OF THE INVENTION

According to the present invention, there is provided an improved friction and gripping composition in which the addition of a small amount of solvent to a mixture of a chlorinated paraffin and a dry dispersing agent, significantly improves the gripping properties of the composition over prior art compositions. A small amount of solvent, which comprises up to and including about 3.0% by weight relative to the total weight of the composition, has been shown to speed up and enhance the adsorption of the inventive composition on the hands, while not adversely affecting the free-flowing properties of the powder. The inventive composition not only results in the formation of a film exhibiting friction on the surface of the hands, but it leads to a film that has a sufficient durability to water, including perspiration, such that it can last for several hours during use in athletic events, for example. While one use for the inventive product is in the sporting or recreation field, it can also be used in household or commercial uses, such as in the corrugation or banking industries.

DETAILED DESCRIPTION OF THE INVENTION

The present invention is directed to a composition in the form of a dry, finely divided powder (defined as at least 95% and, advantageously, 100% passing through a 100 mesh sieve), for improving grip or friction on the hands. The inventive composition improves friction or grip between the hands and a tool or implement.

One of the main ingredients of the inventive composition, chlorinated paraffin, is a fully saturated hydrocarbon generally considered to be a mixture of molecules having from about 18 to about 24 carbon atoms in the chain. The starting paraffin material needs only to chemically meet the requirement that it have from about 18 to about 24 carbon atoms in the chain. It has been found that when a molecule of such size is chlorinated to at least about 60 percent, as well as to about 70 percent or more by weight of chlorine, the molecule is converted to a solid which can be reduced to an extremely finely divided powder form.

The chlorinated paraffin in the inventive composition comprises about 95% percent, by weight, of the total composition. In addition, the chlorinated paraffin-is in an anhydrous condition and finely divided, defined by at least 95% and up to 100% passing through a 100 mesh sieve. An example of the chlorinated paraffin used in the present invention is described in U.S. Pat. No. 3,035,988, the entire teachings of which are herein incorporated by reference.

The effectiveness of the present composition for enhancing gripping when applied to the hands is quite unique in that it has an apparent affinity for the skin which is unexpected, considering the melting point of the solid chlorinated paraffin is of the order of 90°–100° C. Therefore, the formation of a waterproof friction film on the skin is quite surprising, since the formation of the film cannot be attributed to the melting of the compound by body heat. A reasonable explanation for the mechanism action of the chlorinated paraffin on the hands would be that some minor amounts of less highly chlorinated paraffin are present, resulting in a broadened softening range of the chlorinated paraffin component. Accordingly, when the finely divided powder is rubbed over the hands, the less highly chlorinated material softens and induces the adhesion to the skin. The organic end of the chlorinated paraffin molecule, aided by small amounts of solvent which act to soften the chlorinated paraffin component, is strongly adsorbed by the organic surface of the skin. The highly polar end of the component is also similarly strongly attracted to and adsorbed by, the object to be grasped, e.g., a bat, racquet, golf club, or tool. Thus, the improved gripping properties associated with the inventive composition are believed to be a function of the polar molecule ends associated with a chlorinated paraffin, which are believed to lead to optimum attraction and adsorption properties, when the softening range of the chlorinated paraffin is broadened by a small amount of solvent.

The dispersing agent is an inert, extremely high surface area per unit weight material, such as colloidal silica, which not only enhances the flowability of the chlorinated paraffin resin, but permits the distribution of the solvent throughout the chlorinated paraffin without causing agglomeration. While colloidal silica is a useful dispersing agent, as exemplified, infra, other materials which may be used in accordance with the present invention include submicron sized inorganic materials, such as precipitated high surface area aluminosilicate, sold under the name Zeolex® (J.M. Huber, Co.). The inorganic materials used in the inventive composition have a particle size ranging from about 5 to about 15 microns.

In addition, while a useful solvent is perchloroethylene, the solvent may comprise any high solvency fluid, such as trichloroethylene, methyl ethyl ketone, acetone, or amyl acetate. Such solvents act to broaden or extend the softening range of the chlorinated paraffin, further aiding in the formation of the friction film when applied to the hands.

The present invention also relates to a method of making a composition for improving friction or grip on the hands. The method comprises adding up to about 3% solvent to a dispersing agent. After adding the solvent to the dispersing agent, which may be performed by spraying, for example, the combination of dispersing agent, e.g., colloidal silica, and solvent is added to the chlorinated paraffin. The solvent should be added in such a way that it is first diffused throughout the finely divided dispersant, rather than simply being added to the mixture or the chlorinated paraffin. This permits the utilization of the high specific surface area of the dispersant to bring about the introduction of the solvent without causing agglomeration of the chlorinated paraffin.

The specific surface areas of the dispersants according to the present invention are on the order of about 75 to about 380m$^2$/g, depending on the material used. By adding the small amount of solvent used in the present invention such that it is uniformly distributed over the large surface areas of the dispersant, the solvent is brought into uniform contact with the particles of the chlorinated paraffin by first being made to coat the much finer particles of the colloidal silica, which are micron sized particles, which then coat the particles of the chlorinated paraffin. The resulting mixture in then milled to form a powder in which at least 95%, and advantageously 100%, of the powder passes through a 100 mesh sieve. The final powder is completely insoluble in water, tasteless, non-allergenic, and odorless.

Various ranges of components were evaluated in fabricating the inventive composition, with one embodiment comprising from about 97 to about 99% chlorinated paraffin, from about 0.25 to about 1.5% solvent, and from about 0.25 to about 2.0% dispersing agent, such as colloidal silica. The four examples provided in Table 1 are illustrative of the present invention. It has been found that a single dusting or coating of the hands, wherein the composition of the invention is thoroughly rubbed onto their surface at the commencement of a contest or a match, has provided the user with a more than adequate friction treatment of the hands to last through the entire contest, and indeed continued to be effective even after the hands were lightly washed with soap and water.

TABLE 1

| Material | Sample 1 | Sample 2 | Sample 3 | Sample 4 |
| --- | --- | --- | --- | --- |
| Chlorinated paraffin[1] | 99.5 | 99.0 | 98.0 | 96.5 |
| colloidal silica[2] | 0.25 | 0.5 | 1.0 | 2.0 |
| Solvent[3] | 0.25 | 0.5 | 1.0 | 1.5 |

[1]70% chlorinated paraffin supplied by Dover Chemical and sold under the trademark Chlorez LMP.
[2]Supplied by Cabot Corp., and sold under the trademark CAB-O-SIL.
[3]perchloroethylene.

Though the invention has been described with reference to only a limited number of examples, it is to be understood that variants thereof may be practiced without departing from the inventive spirit or scope.

What is claimed is:

1. A friction or grip improving composition for improving friction or grip between the hands and a tool or implement, said composition comprising a chlorinated paraffin, at least one dispersing agent, and at least one solvent, said solvent being present in an amount from about 0.25% up to and including about 3.0% by weight relative to the total weight of the composition, wherein said composition is in the form of a dry powder.

2. The composition of claim 1, wherein said chlorinated paraffin comprises at least about 60% chemically combined chlorine.

3. The composition of claim 2, wherein said chlorinated paraffin comprises at least about 70% chemically combined chlorine.

4. The composition of claim 1, wherein said chlorinated paraffin comprises from about 18 to about 24 carbon atoms.

5. The composition of claim 1, wherein at least 95% of said chlorinated paraffin passes through a 100 mesh sieve.

6. The composition of claim 5, wherein 100% of said chlorinated paraffin passes through a 100 mesh sieve.

7. The composition of claim 1, wherein said at least one dispersing agent is chosen from colloidal silica and aluminosilicate, wherein said aluminosilicate has a particle size ranging from about 5 to about 15 microns.

8. The composition of claim 1, wherein said at least one solvent is chosen from perchloroethylene, trichloroethylene, methyl ethyl ketone, acetone, and amyl acetate.

9. The composition of claim 8, wherein said at least one solvent is present in an amount ranging from about 0.25 to about 2.0% by weight relative to the total weight of the composition.

10. The composition of claim 1 comprising, by weight:
   from about 97 to about 99% chlorinated paraffin;
   from about 0.25 to about 1.5% solvent; and
   from about 0.25 to about 2.0% dispersing agent.

11. The composition of claim 10, wherein said chlorinated paraffin comprises at least about 60% of chemically combined chlorine.

12. The composition of claim 10, wherein said solvent is perchloroethylene.

13. The composition of claim 10, wherein said dispersing agent is colloidal silica or aluminosilicate, wherein said aluminosilicate has a particle size ranging from about 5 to about 15 microns.

14. A method of making a friction or grip improving composition for improving friction or grip between the hands and a tool or implement, said method comprising:
   combining, by weight relative to the total weight of the composition, from about 0.25 to about 3% solvent and from about 0.25 to about 3% dispersing agent;
   mixing the combination of solvent and dispersing agent with chlorinated paraffin in an amount sufficient to complete said composition; and
   milling the resulting mixture to form a powder in which at least 95% of said powder passes through a 100 mesh sleve.

15. The method of claim 14, wherein said chlorinated paraffin comprises at least about 60% chemically combined chlorine.

16. The method of claim 14, wherein said solvent is chosen from perchloroethylene, trichloroethylene, methyl ethyl ketone, acetone, and amyl acetate.

17. The method of claim 14, wherein said dispersing agent comprises at least one compound chosen from colloidal silica and aluminosilicate.

18. The method of claim 14, wherein said chlorinated paraffin is uniformly coated with said solvent by contacting the chlorinated paraffin with a dispersing agent that has been precoated with said solvent.

19. A method of improving friction or grip between the hands and a tool or implement, said method comprising contacting the hands with a dry powder in an amount sufficient to form a film on the hands, said powder comprising a chlorinated paraffin, at least one dispersing agent, and at least one solvent in an amount from about 0.25% up to and including about 3.0% by weight, relative to the total weight of the composition.

20. The method of claim 18, wherein said solvent is chosen from perchloroethylene, trichloroethylene, methyl ethyl ketone, acetone, and amyl acetate.

21. The method of claim 18, wherein said dispersing agent comprises at least one compound chosen from colloidal silica and aluminosilicate, wherein said aluminosilicate has a particle size ranging from about 5 to about 15 microns.

22. The method of claim 14, wherein said chlorinated paraffin is present in an amount of at least about 95% by weight relative to the total weight of the composition.

\* \* \* \* \*

UNITED STATES PATENT AND TRADEMARK OFFICE
CERTIFICATE OF CORRECTION

PATENT NO. : 6,656,257 B2  Page 1 of 1
DATED : December 2, 2003
INVENTOR(S) : Robert S. Cohen It is certified that error appears in the above-identified patent and that said Letters Patent is hereby corrected as shown below:

Column 5,
Line 33, "sleve" should read -- sieve --.

Signed and Sealed this

Sixteenth Day of March, 2004

JON W. DUDAS
*Acting Director of the United States Patent and Trademark Office*